United States Patent [19]

Hoelderich et al.

[11] Patent Number: 4,931,564
[45] Date of Patent: Jun. 5, 1990

[54] PREPARATION OF CYANOPYRIDINES

[75] Inventors: Wolfgang Hoelderich, Frankenthal; Norbert Goetz, Worms, both of Fed. Rep. of Germany

[73] Assignee: BASF Aktiengesellschaft, Ludwigshafen, Fed. Rep. of Germany

[21] Appl. No.: 279,041

[22] Filed: Dec. 2, 1988

[30] Foreign Application Priority Data

Dec. 4, 1987 [DE] Fed. Rep. of Germany ....... 3741159

[51] Int. Cl.$^5$ .......................................... C07D 213/57
[52] U.S. Cl. ..................................... 546/286; 546/250
[58] Field of Search ................................ 546/286, 250

[56] References Cited

U.S. PATENT DOCUMENTS

| | | | |
|---|---|---|---|
| 4,220,783 | 9/1980 | Chang et al. | 546/251 |
| 4,401,637 | 8/1983 | Marosi e al. | 423/329 |
| 4,512,961 | 4/1985 | Scherzer et al. | 423/328 |

FOREIGN PATENT DOCUMENTS

| | | | |
|---|---|---|---|
| 0046504 | 3/1982 | European Pat. Off. | 502/60 |
| 0131887 | 1/1986 | European Pat. Off. | 546/251 |
| 2023158 | 11/1970 | Fed. Rep. of Germany | 546/251 |
| 2224160 | 2/1973 | Fed. Rep. of Germany | 502/208 |
| 2151417 | 4/1973 | Fed. Rep. of Germany | 502/203 |
| 2239801 | 2/1974 | Fed. Rep. of Germany | 502/226 |
| 2449340 | 4/1976 | Fed. Rep. of Germany | 546/251 |
| 2703070 | 7/1978 | Fed. Rep. of Germany | 546/251 |
| 2819196 | 11/1979 | Fed. Rep. of Germany | 546/251 |
| 1273826 | 9/1961 | France | 546/251 |

Primary Examiner—Alan L. Rotman
Attorney, Agent, or Firm—Keil & Weinkauf

[57] ABSTRACT

Cyanopyridines of the formula

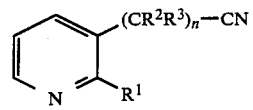

are prepared by reacting acrolein and an alkanal

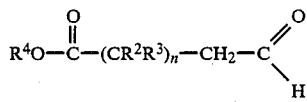

or its acetal or ketone of the formula

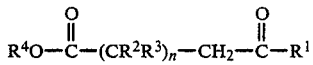

where $R^1$, $R^2$ and $R^3$ may be identical or different and are each hydrogen, alkyl of 1 to 6 carbon atoms or aryl and $R^4$ is alkyl and n is 0–11, with ammonia in the presence of a zeolite as a catalyst. The reaction is preferably carried out in the gas phase.

8 Claims, No Drawings

PREPARATION OF CYANOPYRIDINES

The present invention relates to a process for the preparation of cyanopyridines by catalytic reaction of a mixture of acrolein and an alkanal or ketone with ammonia in the presence of a zeolite catalyst.

It is known that 3-methylpyridine is formed in the reaction of acrolein with ammonia in the gas phase in the presence of a catalyst. The catalysts used are in particular compounds of the elements Al, F and O, which have been pretreated with oxygen at from 550° to 1200° C. and additionally contain one or more elements of the second, third or fourth group of the Periodic Table (German Laid-Open Application DOS No. 2,151,417) or two or more elements of the second, fourth, fifth or sixth group of the Periodic Table (German Laid-Open Application DOS No. 2,224,160) or one or more elements of the second main group of the Periodic Table (German Laid-Open Application DOS No. 2,239,801). It is also known, that when when the reaction is carried out in a fluidized bed, the acrolein must be fed into the fluidized bed separately from the ammonia (German Laid-Open Application DOS No. 2,449,340). The disadvantage of this process is that a considerable amount of pyridine is formed in addition to 3-methylpyridine, and the yield of 3-methylpyridine is less than 30%.

It is also known that 3-methylpyridine can be prepared by reacting a mixture of acrolein and propionaldehyde with ammonia. The catalysts used are alumina, silica or silica mixed with from 5 to 50% of alumina, with or without the addition of oxides of further elements (French Pat. No. 1,273,826). In this process, the yield of 3-methylpyridine is 53%.

Compared with the process described above, in German Pat. No. 2,703,070 the yield of 3-methylpyridine is increased to 61% by using finely divided aluminum silicates having a BET surface area of 200-800 m²/g.

German Pat. No. 2,819,196 discloses the preparation of pyridines substituted by aromatic and heteroaromatic radicals. Yields of up to 65% of phenylpyridine are obtained over compounds of the elements Al, F and O, which have been pretreated at 550°-1200° C. and additionally contain an element of group 2, 3 or 4 of the Periodic Table.

Lanthanum-doped molecular sieves (German Pat. No. 2,023,158) are also only moderately effective catalysts and therefore give only low yields. A further disadvantage here is that the reaction is restricted only to the use of acrolein and is carried out in the presence of oxygen, and a mixture of 43 mol % of pyridine and 22 mol % of 3-methylpyridine is obtained.

U.S. Pat. No. 4,220,783 describes a process for the preparation of pyridine and picoline over the aluminosilicate zeolite ZSM 5, from $C_2$–$C_4$-aldehydes or $C_3$–$C_5$-ketones and ammonia. The reaction is carried out in the presence of methanol or water. In the presence of formaldehyde, a larger amount of pyridine is formed. The catalyst is very rapidly deactivated; 93% conversion is obtained after 0.7 hour and only 78% conversion after 3 hours. The yield of 7.7% of pyridine and 59.6% of picoline is also unsatisfactory. The other catalysts mentioned give even poorer yields; a larger amount of hydrocarbons and high-boiling products is formed.

European Pat. No. 131,887 discloses that acidic aluminosilicate zeolites of the pentasil type having a constraint index of from 1 to 12 give better results for the preparation of alkylpyridines when used in a fluidized bed than in a fixed bed. In the reaction of acetaldehyde with formaldehyde, the maximum total yield, based on all the pyridines obtained, is 89.8%, the pyridine/β-picoline ratio being 2:1. However, this high value is found only between the first and second hour of the reaction. The reaction temperature should be higher than 450° C. and the residence time over the catalyst should be more than 2.5 sec. The disadvantages of this process are that the catalyst has to be regenerated after only 4 hours and the product spectrum cannot be kept constant, and the reaction has to be carried out by the technically complicated fluidized-bed method in order to obtain high yields.

It is an object of the present invention selectively to synthesize pyridines substituted by a cyano group from readily obtainable starting materials in the presence of a catalyst which possesses high activity and a long life.

We have found that this object is achieved and that cyanopyridines of the formula (I)

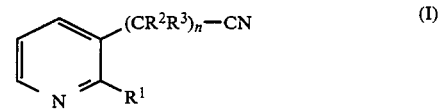

are obtained in good yields, and with long catalyst lives, from readily obtainable starting materials by reacting acrolein and an alkanal of the formula (II) or its acetal or ketone of the formula (III)

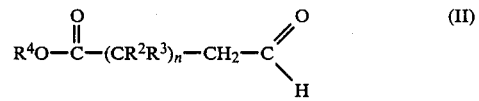

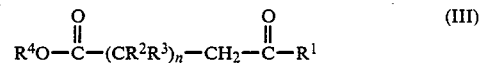

where $R^1$, $R^2$ and $R^3$ may be identical or different and are each hydrogen, alkyl of 1 to 6 carbon atoms or aryl and $R^4$ is alkyl, with ammonia, if the reaction is carried out in the presence of a zeolite as a catalyst.

The reaction is preferably effected in the gas phase at from 100° to 500° C. Examples of suitable starting compounds are methyl acetoacetate and propyl acetoacetate.

For example, in the case of 2-methyl-3-cyanopyridine, the reaction can be represented by the following equation:

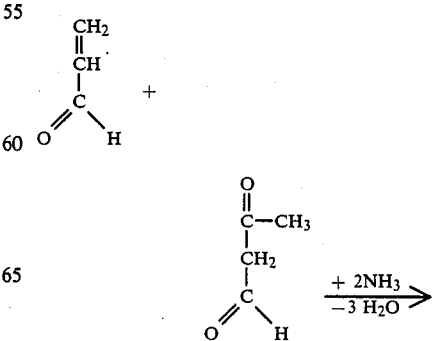

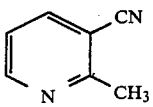

The catalysts used for the novel process are acidic zeolite catalysts. Zeolites are crystalline aluminosilicates which have a highly ordered structure with a rigid three-dimensional network of $SiO_4$ and $AlO_4$ tetrahedra which are bonded by common oxygen atoms. The ratio of Si and Al atoms to oxygen is 1:2. The electrovalency of the aluminum-containing tetrahedra is balanced by the inclusion of cations in the crystal, for example of an alkali metal ion or hydrogen ion. Cation exchange is possible. The voids between the tetrahedra are occupied by water molecules prior to dehydration by drying or calcination.

In the zeolites, instead of aluminum it is also possible to incorporate other elements, such as B, Ga, Fe, Cr, V, As, Sb, Bi or Be, or a mixture of these in the framework, or the silicon can be replaced by a tetravalent element, such as Ge, Ti, Zr or Hf.

Depending on their structure, zeolites are divided into various groups. For example, the zeolite structure is formed by chains of tetrahedra in the mordenite group or by sheets of tetrahedra in the chabasite group, while in the faujasite group the tetrahedra are arranged to form polyhedra, for example in the form of a cubooctahedron, which is composed of 4-membered rings and 6-membered rings. Depending on the bonding of the cubooctahedra, which gives rise to cavities and pores of different sizes, a distinction is made between zeolites of type A, L, X or Y.

In particular, zeolites from the mordenite group or fine-pore zeolites of the erionite or chabasite type or zeolites of the faujasite type, for example Y, X or L zeolites are used for the novel process. This group of zeolites includes the ultrastable zeolites of the faujasite type, i.e. dealuminated zeolites (U.S. Pat. No. 4,512,961).

Particularly advantageous zeolites are those of the pentasil type. These have, as a common basic building block, a 5-membered ring composed of $SiO_4$ tetrahedra. They possess a high $SiO_2/Al_2O_3$ ratio and pore sizes which are between those of the zeolites of type A and those of type X or Y.

These zeolites may have different chemical compositions. They are aluminosilicate, borosilicate, iron silicate, beryllium silicate, gallium silicate, chromium silicate, arsenosilicate, antimony silicate and bismuth silicate zeolites or mixtures of these, and aluminogermanate, borogermanate, gallium germanate and iron germanate zeolites or mixtures of these. The aluminosilicate, borosilicate and iron silicate zeolites of the pentasil type are particularly suitable for the novel process. The aluminosilicate zeolite is prepared, for example, from an aluminum compound, preferably $Al(OH)_3$ or $Al_2(SO_4)_3$, and a silicon component, preferably finely divided silica, in aqueous amine solution, in particular in polyamines, such as 1,6-hexanediamine or 1,3-propanediamine or triethylenetetramine solution with or, in particular, without the addition of an alkali or alkaline earth, at from 100° to 200° C. under autogenous pressure. These include the isotactic zeolites according to German Laid-Open Application DOS No. 3,006,471 and European Pat. No. 46,504. The aluminosilicate zeolites obtained have an $SiO_2/Al_2O_3$ ratio of from 10 to 40,000, depending on the amounts of starting materials chosen. These aluminosilicate zeolites can also be synthesized in an ether medium, such as diethylene glycol dimethyl ether, in an alcoholic medium, such as methanol or butane-1,4-diol, or in water.

Borosilicate zeolites are synthesized, for example, at from 90° to 200° C. under autogenous pressure by reacting a boron compound such as $H_3BO_3$, with a silicon compound, preferably finely divided silica, in aqueous amine solution, in particular in 1,6-hexanediamine or 1,3-propanediamine or triethylenetetramine solution, with or, in particular, without the addition of an alkali or alkaline earth. The isotactic zeolites according to German Laid-Open Application DOS No. 3,006,471 and European Pat. No. 46,504 can also be used. Such borosilicate zeolites can also be prepared by carrying out the reaction not in aqueous amine solution but in solution in an ether, for example in diethylene glycol dimethyl ether, or in alcoholic solution, for example hexane-1,6-diol.

Iron silicate zeolites are obtained from an iron compound, preferably $Fe_2(SO_4)_3$, and a silicon compound, preferably finely divided silica, in aqueous amine solution, in particular in 1,6-hexanediamine, with or without the addition of an alkali or alkaline earth, at from 100° to 220° C. under autogenous pressure.

The silicon-rich zeolites which can be used ($SiO_2/Al_2O_3 \geq 10$) include the ZSM types, such as ZSM-5, ZSM-8, ZSM-12, ZSM-21, ZSM-22, ZSM-23, ZSM-25, ZSM-34, ZSM-35 and ZSM-48.

Ferrierite, as a crystalline zeolite, and NU-1 and Silicalit®, a molecular sieve, i.e. a silica polymorph, are also suitable.

The aluminosilicate, borosilicate and iron silicate zeolites thus prepared can be isolated, dried at from 100° to 160° C., preferably 110° C., and calcined at from 450° to 550° C., preferably 500° C., and then molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 90:5, preferably 75:25, silica, preferably finely divided $SiO_2$, mixtures of finely divided $SiO_2$ and finely divided $Al_2O_3$, $TiO_2$, $ZrO_2$ and clay. After the molding procedure, the extrudates or pellets are dried at 110° C. for 16 hours and calcined at 500° C. for 16 hours.

Advantageous catalysts are also obtained if the aluminosilicate or borosilicate zeolite isolated is molded directly after drying and is not subjected to calcination until after the molding procedure. The aluminosilicate and borosilicate zeolites prepared can be used in pure form, without a binder, as extrudates or pellets, examples of extrusion or peptizing assistants used being ethylcellulose, stearic acid, potato starch, formic acid, oxalic acid, acetic acid, nitric acid, ammonia, amines, silicoesters and graphite or mixtures of these.

If, because of its method of preparation, the zeolite is not in the catalytically active, acidic H form but, for example, in the Na form, the latter can be completely or partially converted into the desired H form by ion exchange, for example with ammonium ions, and subsequent calcination, or by treatment with acids.

If, when the zeolite catalysts are used according to the invention, deactivation occurs as a result of coking, it is advisable to regenerate the zeolites by burning off the coke deposit with air or with an air/$N_2$ mixture at from 400° to 550° C., in particular 500° C. As a result, the zeolites regain their initial activity.

By precoking, it is possible to adjust the activity of the catalyst to obtain optimum selectivity with respect to the desired reaction product.

In order to achieve very high selectivity, high conversion and long catalyst lives, it is advantageous to modify the zeolites. In a suitable method for modifying the catalysts, for example, the unmolded or molded zeolites are doped with metal salts by ion exchange or by impregnation. The metals used are alkali metals, such as Li, Cs or K, alkaline earth metals, such as Mg, Ca or Sr, metals of main groups 3, 4 and 5, such as Al, Ga, Ge, Sn, Pb or Bi, transition metals of subgroups 4–8, such as Ti, Zr, V, Nb, Cr, Mo, W, Mn, Re, Fe, Ru, Os, Co, Rh, Ir, Ni, Pd or Pt, transition metals of subgroups 1 and 2, such as Cu, Ag or Zn, or rare earth metals, such as La, Ce, Pr, Nd, Er, Yb and U.

Advantageously, the doping is carried out by initially taking the molded zeolites in a riser tube and passing an aqueous or ammoniacal solution of a halide or of a nitrate of the abovementioned metals over the said zeolites at from 20° to 100° C. Ion exchange of this type can be carried out on the hydrogen, ammonium or alkali metal form of the zeolite. In another possible method for applying metals to the zeolites, the zeolite material is impregnated with a halide, a nitrate or an oxide of the metals in aqueous, alcoholic or ammoniacal solution. Both ion exchange and impregnation are followed by at least a drying step or alternatively by repeated calcination.

In a possible embodiment, for example, $Cu(NO_3)_2.3H_2O$ or $Ni(NO_3)_2.6H_2O$ or $Ce(NO_3)_3.6H_2O$ or $La(NO_3)_2.6H_2O$ or $Cs_2CO_3$ is dissolved in water and this solution is used to impregnate the molded or unmolded zeolite for a certain time, i.e. about 30 minutes. The supernatant solution is freed from water in a rotary evaporator. Thereafter, the impregnated zeolite is dried at about 150° C. and calcined at about 550° C. This drying process can be carried out several times in succession in order to obtain the desired metal content.

It is also possible to prepare an aqueous $Ni(NO_3)_2$ solution or ammoniacal $Pd(NO_3)_2$ solution and to suspend the pure zeolite powder therein at from 40° to 100° C. for about 24 hours, while stirring. The product is filtered off, dried at about 150° C. and calcined at about 500° C., and the zeolite material thus obtained is then further processed with or without binders to give extrudates, pellets or fluidizable material.

The zeolite in the H form or ammonium form or alkali metal form can be subjected to ion exchange by a procedure in which the zeolite, in the form of extrudates or pellets, is initially taken in a column and an aqueous $Ni(NO_3)_2$ solution or ammoniacal $Pd(NO_3)_2$ solution is circulated over the said zeolite at slightly elevated temperatures of from 30° to 80° C. for from 15 to 20 hours. The product is then washed thoroughly with water, dried at about 150° C. and calcined at about 550° C. In the case of some metal-doped zeolites, aftertreatment with hydrogen is advantageous.

In another possible method of modification, the molded or unmolded zeolite material is subjected to treatment with acids, such as hydrochloric acid, hydrofluoric acid and phosphoric acid, and/or steam. The procedure can be used in which zeolites in powder form are treated with 1N phosphoric acid for 1 hour at 80° C. After the treatment, the product is washed with water, dried at 110° C. for 16 hours and calcined at 500° C. for 20 hours. In another procedure, zeolites, before or after they have been molded with binders, are treated with 3–25, in particular 12–20, % strength by weight aqueous hydrochloric acid, for example for from 1 to 3 hours at from 60° to 80° C. The zeolite thus treated is then washed with water, dried, and calcined at from 400° to 500° C.

In a particular embodiment of the acid treatment, the zeolite material, before it has been molded, is treated at elevated temperatures with 0.001–2N, preferably 0.05–0.5N, hydrofluoric acid, for example by refluxing for from 0.5 to 5, preferably from 1 to 3, hours. The zeolite material is isolated, for example by filtering it off and washing it thoroughly, and is then advantageously dried at from 100° to 160° C. and calcined at from 450° to 600° C. In a further preferred embodiment of the acid treatment, the zeolite material is molded with a binder and then treated preferably with from 12 to 20% strength by weight hydrochloric acid at elevated temperatures, advantageously at from 50° to 90° C., in particular from 60° to 80° C., for from 0.5 to 5 hours. The zeolite material is then washed thoroughly and advantageously dried at from 100° to 160° C. and calcined at from 450° to 600° C. An HF treatment may also be followed by an HCl treatment.

In another procedure, zeolites can be modified by applying phosphorus compounds, such as trimethyl phosphate, trimethylphosphine oxide or primary, secondary or tertiary sodium phosphate. Treatment with primary sodium phosphate has proven advantageous. In this procedure, the zeolites, in the form of extrudates, pellets or fluidizable material, are impregnated with aqueous $NaH_2PO_4$ solution, dried at 110° C. and calcined at 550° C.

The catalysts described here can be used alternatively in the form of 2–4 mm extrudates, tablets of 3–5 mm diameter or chips having particle sizes of from 0.1 to 0.5 mm, or as fluidized catalysts.

In the novel process, a molar ratio of acrolein to alkanal or ketone of the formula (II) or (III), respectively, to $NH_3$ of 1:1–2:1–15, preferably 1:1:3–8, is advantageously maintained. The reaction is advantageously carried out in the gas phase at from 100° to 500° C., advantageously from 200° to 450° C., in particular from 250° to 400° C., as a rule under from 0.1 to 100 bar, in particular from 0.5 to 10 bar.

In the reaction of acrolein and alkanal of the formula (II) or ketone of the formula (III) with ammonia over the catalyst described above in the gas phase, a weight hourly space velocity (WHSV) of from 0.1 to 20, in particular from 1 to 10, g of mixture of acrolein and alkanal/ketone of the formula (II) or (III) per g of catalyst per hour (WHSV) is advantageously maintained.

The reactions in the gas phase can be carried out in a fixed bed or in a fluidized bed. It is also possible to effect the reaction in the liquid phase (suspension, trickle-bed or liquid-phase procedure) at from 20° to 200° C.

The reaction can be carried out batchwise but is preferably effected continuously under atmospheric, reduced or superatmospheric pressure.

Sparingly volatile or solid starting materials are used in dissolved form, for example in solution in tetrahydrofuran, toluene or petroleum ether. In general, the starting material can be diluted with such solvents or with inert gases, such as $N_2$, Ar or steam.

After the reaction, the resulting products are isolated from the reaction mixture by a conventional method, for example by distillation; unconverted starting materials are, if desired, recycled to the reaction according to the invention.

The cyanopyridines obtainable by the novel process are versatile intermediates.

EXAMPLES 1 to 3

The reaction in the gas phase is carried out under isothermal conditions in a tube reactor (coil, 0.6 cm internal diameter, 90 cm length) in the course of not less than 6 hours. The reaction products are isolated and characterized by conventional methods. Quantitative determination of the reaction products and of the starting materials is carried out by a known gas chromatographic method.

The catalysts used for the novel process are:

Catalyst A

The borosilicate zeolite of the pentasil type is prepared in a hydrothermal synthesis from 640 g of finely divided $SiO_2$, 122 g of $H_3BO_3$ and 8,000 g of an aqueous 1,6-hexanediamine solution (weight ratio 50:50) at 170° C. under autogenous pressure in a stirred autoclave. The crystalline reaction product is filtered off, washed thoroughly and then dried at 100° C. for 24 hours and calcined at 500° C. for 24 hours. This borosilicate zeolite is composed of 94.2% by weight of $SiO_2$ and 2.3% by weight of $B_2O_3$.

This material is molded with boehmite in a weight ratio of 60:40 to give 2 mm extrudates, which are dried at 110° C. for 16 hours and calcined at 500° C. for 24 hours.

Catalyst B 100 g of the borosilicate zeolite used in catalyst A are treated with 280 ml of a 0.1N HF at 90° C., and the product is filtered off and then dried at 160° C. This product is molded with amorphous aluminosilicate (25% by weight of $Al_2O_3$ and 75% by weight of $SiO_2$) in a weight ratio of 60:40 to give 2 mm extrudates, which are dried at 110° C. for 16 hours and calcined at 500° C. for 16 hours.

Catalyst C

Commercial NaY zeolite is molded with boehmite in a weight ratio of 60:40 to give 2 mm extrudates, which are dried at 110° C. for 16 hours and calcined at 540° C. for 24 hours. These extrudates are subjected to ion exchange with a 20% strength aqueous a $(NO_3)_2$ solution at 80% for 2 hours. After the product has been dried at 110° C. and calcined at 500° C., the La content should be 7.1% by weight and Na content 1.1% by weight. After intermediate calcination, ion exchange can be repeated until the above La and Na contents are obtained.

The test results and reaction conditions are summarized in the Table below. Byproducts are, for example, 2- and 3-methylpyridine, methyl 2-methylnicotinate and 2-methylnicotinamide.

TABLE

| | Acrolein (I) + methyl acetoacetate (II) + $NH_3 \rightarrow$ 2-methyl-3-cyanopyridine (III) + $H_2O$ + $CH_3OH$ + $H_2$ | | |
|---|---|---|---|
| Example | 1 | 2 | 3 |
| Catalyst | A | B | C |
| Temperature °C. | 350 | 350 | 350 |
| WHSV $h^{-1}$ | 2 | 2 | 2 |
| Molar ratio | 1:1:6 | 1:1:6 | 1:1:6 |
| Conversion % I + II | 100 | 100 | 100 |
| Selectivity % III | 56.7 | 61.5 | 48.9 |

We claim:

1. A process for the preparation of 2-methyl-3-cyanopyridine which comprises: reacting acrolein and methyl acetoacetate with ammonia in the presence of a zeolite as a catalyst.

2. The process of claim 1, wherein the reaction is carries out in the gas phase at a temperature of from 100° to 500° C.

3. The process of claim 1, wherein the catalyst used is a zeolite of the pentasil type.

4. The process of claim 1, wherein the catalyst used is a borosilicate zeolite of the pentasil type.

5. The process of claim 1, wherein the catalyst used is an iron silicate zeolite of the pentasil type.

6. The process of claim 1, wherein the catalyst used is an aluminosilicate zeolite of the pentasil type.

7. The process of claim 1, wherein the catalyst used is an aluminosilicate zeolite of the faujasite type.

8. The process of claim 1, wherein the catalyst used is a zeolite which has been doped with alkali metals or with alkaline earth metals or with transition metals or with rare earth metals.

* * * * *